United States Patent
Parkin et al.

(10) Patent No.: US 11,111,199 B2
(45) Date of Patent: Sep. 7, 2021

(54) METHODS FOR PREPARING FORMALDEHYDE FROM CARBON DIOXIDE

(71) Applicant: THE TRUSTEES OF COLUMBIA UNIVERSITY IN THE CITY OF NEW YORK, New York, NY (US)

(72) Inventors: Gerard Parkin, New York, NY (US); Zack Strater, New York, NY (US); Michael Rauch, Short Hills, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/833,483

(22) Filed: Mar. 27, 2020

(65) Prior Publication Data
US 2020/0317594 A1 Oct. 8, 2020

Related U.S. Application Data

(60) Provisional application No. 62/831,009, filed on Apr. 8, 2019.

(51) Int. Cl.
| | |
|---|---|
| *C07C 45/00* | (2006.01) |
| *B01J 31/00* | (2006.01) |
| *C07C 45/51* | (2006.01) |
| *B01J 31/18* | (2006.01) |
| *B01J 31/14* | (2006.01) |
| *C07C 47/04* | (2006.01) |

(52) U.S. Cl.
CPC ........... *C07C 45/515* (2013.01); *B01J 31/146* (2013.01); *B01J 31/1815* (2013.01); *B01J 2531/22* (2013.01); *C07C 47/04* (2013.01)

(58) Field of Classification Search
CPC .............................. C07C 45/515; B01J 31/146
See application file for complete search history.

(56) References Cited

PUBLICATIONS

Liger et al. Direct [11C] Methylation of Amines from [11C] CO2 for the Synthesis of PET Radiotracers. European Journal of Organic Chemistry, 6434-6438. (Year: 2015).*
Rios et al. Selective reduction of carbon dioxide to bis(silyl) acetal catalyzed by PBP-supported nickel complex. Chemical Communication, vol. 52, 2114-2117. (Year: 2016).*
Huang et al. The Catalytic Role of N-Heterocyclic Carbene in a Metal-Free Conversion of Carbon Dioxide into Methanol: A Computational Mechanism Study. Journal of the American Chemical Society, vol. 132, 12388-12396. (Year: 2010).*
Allen, et al. "Metal-catalysed isotopic exchange labelling: 30 years of experience in pharmaceutical R&D" J. Label. Compd. Radiopharm. 2010, 53, 731-738.
Antoni, G. "Development of carbon-11 labelled PET tracers—Radiochemical and technological challenges in a historic perspective" J. Label. Compd. Radiopharm. 2015, 58, 65-72.
Aresta, M., Carbon Dioxide as Chemical Feedstock. (2010) Wiley-VCH Verlag GmbH & Co. KGaA, online ISBN: 9783527629916.
Atzrodt, et al. "Deuterium- and tritium-labelled compounds: Applications in the life sciences" Angew. Chem. Int. Edit. 2018, 57, 1758-1784.
Boersema, et al. "Multiplex peptide stable isotope dimethyl labeling for quantitative proteomics" Nat. Protoc. 2009, 4, 484-494.
Bragg, et al. "New trends and applications in carboxylation for isotope chemistry" J. Label. Compd. Radiopharm. 2018, 61, 934-948.
Burgos-Barragan, et al. "Mammals divert endogenous genotoxic formaldehyde into one-carbon metabolism" Nature 2017, 548, 549-554.
Chokkathukalam, et al. "Stable isotope-labeling studies in metabolomics: new insights into structure and dynamics of metabolic networks" Bioanalysis 2014, 6, 511-524.
Dahl, et al. "New methodologies for the preparation of carbon-11 labeled radiopharmaceuticals" Clin. Transl. Imaging 2017, 5, 275-289.
Dao, et al. "Hydromethylation of unactivated olefins" J. Am. Chem. Soc. 2015, 137, 8046-8049.
Del Vecchio, et al. "Late-stage isotopic carbon labeling of pharmaceutically relevant cyclic ureas directly from CO2" Angew. Chem. Int. Edit. 2018, 57, 9744-9748.
Elmore, C. S. "The use of isotopically labeled compounds in drug discovery" Ann. Rep. Med. Chem. 2009, 44, 515-534.
Fraga, et al. "Climatic suitability of Portuguese grapevine varieties and climate change adaptation," Int. J. Climatol. (2015).
Gant, T. G. "Using deuterium in drug discovery: Leaving the label in the drug" J. Med. Chem. 2014, 57, 3595-3611.
Haywood, et al. "Ammonium [11C]thiocyanate: revised preparation and reactivity studies of a versatile nucleophile for carbon-11 radiolabelling" MedChemComm 2018, 9, 1311-1314.
Hsu, J. L.; Huang, S. Y.; Chen, S. H. "Dimethyl multiplexed labeling combined with microcolumn separation and MS analysis for time course study in proteom ics" Electrophoresis 2006, 27, 3652-3660.
Isin, E. M.; Elmore, C. S.; Nilsson, G. N.; Thompson, R. A.; Weidolf, L. "Use of radiolabeled compounds in drug metabolism and pharmacokinetic studies" Chem. Res. Toxicol. 2012, 25, 532-542.
Kingston, C.; Wallace, M. A.; Allentoff, A. J.; deGruyter, J. N.; Chen, J. S.; Gong, S. X.; Bonacorsi, S.; Baran, P. S. "Direct carbon isotope exchange through decarboxylative carboxylation" J. Am. Chem. Soc. 2019, 141, 774-779.

(Continued)

*Primary Examiner* — Sikarl A Witherspoon
(74) *Attorney, Agent, or Firm* — Bryan Cave Leighton Paisner LLP

(57) ABSTRACT

The present disclosure provides, inter alia, methods for preparing formaldehyde from carbon dioxide using bis(silyl) acetals, methods for incorporating carbon derived from carbon dioxide into a complex organic molecule derived from formaldehyde using bis(silyl)acetals, and methods for generating an isotopologue of a complex organic molecule derived from formaldehyde using bis(silyl)acetals.

30 Claims, 5 Drawing Sheets
(5 of 5 Drawing Sheet(s) Filed in Color)

(56) References Cited

PUBLICATIONS

Liger, F.; Eijsbouts, T.; Cadarossanesaib, F.; Tourvieille, C.; Le Bars, D.; Billard, T. "Direct [11C]methylation of amines from [11C]CO2 for the synthesis of PET radiotracers" Eur. J. Org. Chem. 2015, 6434-6438.

Liu, Q., Wu, L., Jackstell, R. et al. Using carbon dioxide as a building block in organic synthesis. Nat Commun 6, 5933 (2015).

Maxwell, B. D. "New radical methods for the potential synthesis of carbon-13 and carbon-14 labeled complex products" J. Label. Compd. Radiopharm. 2018, 61, 1024-1035.

Roberson, "Review of methods to assign the nuclear magnetic resonance peaks of reductively methylated proteins" Anal. Biochem. 2014, 466, 76-82.

Roeda, D.; Crouzel, C. 111C]Formaldehyde revisited: Considerable concurrent [11C]formic acid formation in the low-temperature conversion of [11C]carbon dioxide into [11C]formaldehyde Appl. Radiat. Isot. 2001, 54, 935-939.

Scott, P. J. H. "Methods for the incorporation of carbon-11 to generate radiopharmaceuticals for pet imaging" Angew. Chem. Int. Edit. 2009, 48, 6001¬6004.

Taddei, et al. "Recent progress in [C-11]carbon dioxide ([C-11]CO2) and [C-11]carbon monoxide ([C-11]C0) chemistry" J. Label. Compd. Radiopharm. 2018, 61, 237-251.

Valette, et al. "Experimental strategies for in vivo 13C NMR spectroscopy" Anal. Biochem. 2017, 529, 216-228.

* cited by examiner

METHODS FOR PREPARING FORMALDEHYDE FROM CARBON DIOXIDE

CROSS REFERENCE TO RELATED APPLICATIONS

The present application claims benefit of U.S. Provisional Patent Application Ser. No. 62/831,009, filed on Apr. 8, 2019, which application is incorporated by reference herein in its entirety.

GOVERNMENT FUNDING

This invention was made with government support under grant nos. DE-SC0019204 and DE-FG02-93ER14339 awarded by Department of Energy (DOE). The government has certain rights in the invention.

FIELD OF DISCLOSURE

The present disclosure provides, inter alia, methods for preparing formaldehyde from carbon dioxide.

BACKGROUND OF THE DISCLOSURE

The efficient utilization of carbon dioxide as a renewable $C_1$ source for the synthesis of value-added organic chemicals and fuels is not only of intrinsic value, but also offers potential for abating the increasing levels of carbon dioxide in the atmosphere (Aresta, 2010; Liu et al. 2015; Fraga et al. 2015). However, $CO_2$ is thermodynamically very stable and kinetically resistant to many transformations, which presents a major impediment to achieving this objective.

Accordingly, there is a need for the exploration of various means to convert carbon dioxide to valuable organic chemicals under ambient conditions, and to synthesize isotopically labeled formaldehyde. This disclosure is directed to meet these and other needs.

SUMMARY OF THE DISCLOSURE

It has been previously disclosed that, under ambient conditions, main group metal catalysts can be utilized to convert carbon dioxide and hydrosilane into a bis(silyl) acetal, $H_2C(OSiR_3)_2$. The present disclosure relates to $H_2C(OSiR_3)_2$ (R=Ph), which can be isolated as a crystalline solid, and can be used (a) to generate formaldehyde under a variety of conditions and (b) as a direct surrogate for formaldehyde in many transformations. This provides a means to incorporate carbon derived from carbon dioxide into a variety of organic chemicals.

Accordingly, one embodiment of the present disclosure is a method for preparing formaldehyde from carbon dioxide, comprising the steps of: (a) obtaining a bis(silyl)acetal; and (b) generating formaldehyde by any one of the following: (i) adding a fluoride compound to a solution of the bis(silyl) acetal in a solvent; or (ii) reaction of the bis(silyl)acetal with water in a d solvent; or (iii) reaction of the bis(silyl)acetal with an acid in a solvent.

Another embodiment of the present disclosure is a method for completing a transformation that involves formaldehyde by substituting formaldehyde with a bis(silyl)acetal.

A further embodiment of the present disclosure is a method for incorporating carbon derived from carbon dioxide into a complex organic molecule derived from formaldehyde, comprising the steps of: (a) obtaining a bis(silyl) acetal by the reaction between carbon dioxide and a silane in the presence of a compound prepared from a multidentate ligand having the structure of:

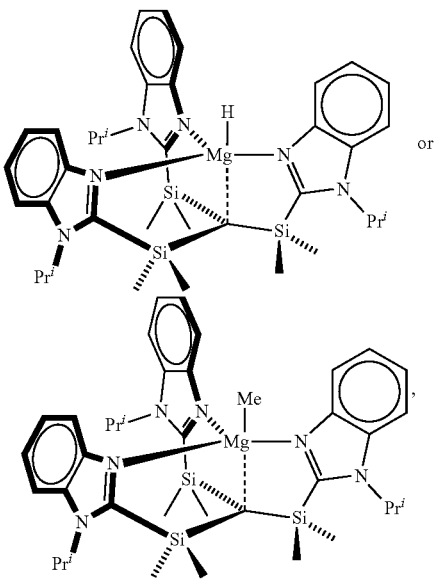

and $B(C_6F_5)_3$, wherein the silane is $R_3SiH$ and R is selected from H, alkyl and aryl; and (b) substituting formaldehyde with the bis(silyl)acetal in a reaction that generates the complex organic molecule.

Still another embodiment of the present disclosure is a method for generating an isotopologue of a complex organic molecule derived from formaldehyde, comprising the steps of: (a) generating isotope-labeled bis(silyl)acetal according to the methods disclosed herein by using isotope-labeled carbon dioxide and/or isotope-labeled silane in the reaction mixture; and (b) generating the isotopologue of the complex organic molecule by using the isotope-labeled bis(silyl) acetal obtained in step (a).

Another embodiment of the present disclosure is a probe, such as, e.g., a positron emission tomography (PET) probe obtained by the methods disclosed herein.

Another embodiment of the present disclosure is a method for carrying out a chemical reaction with a formaldehyde surrogate comprising replacing formaldehyde in the chemical reaction with a bis(silyl)acetal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Figure 1:
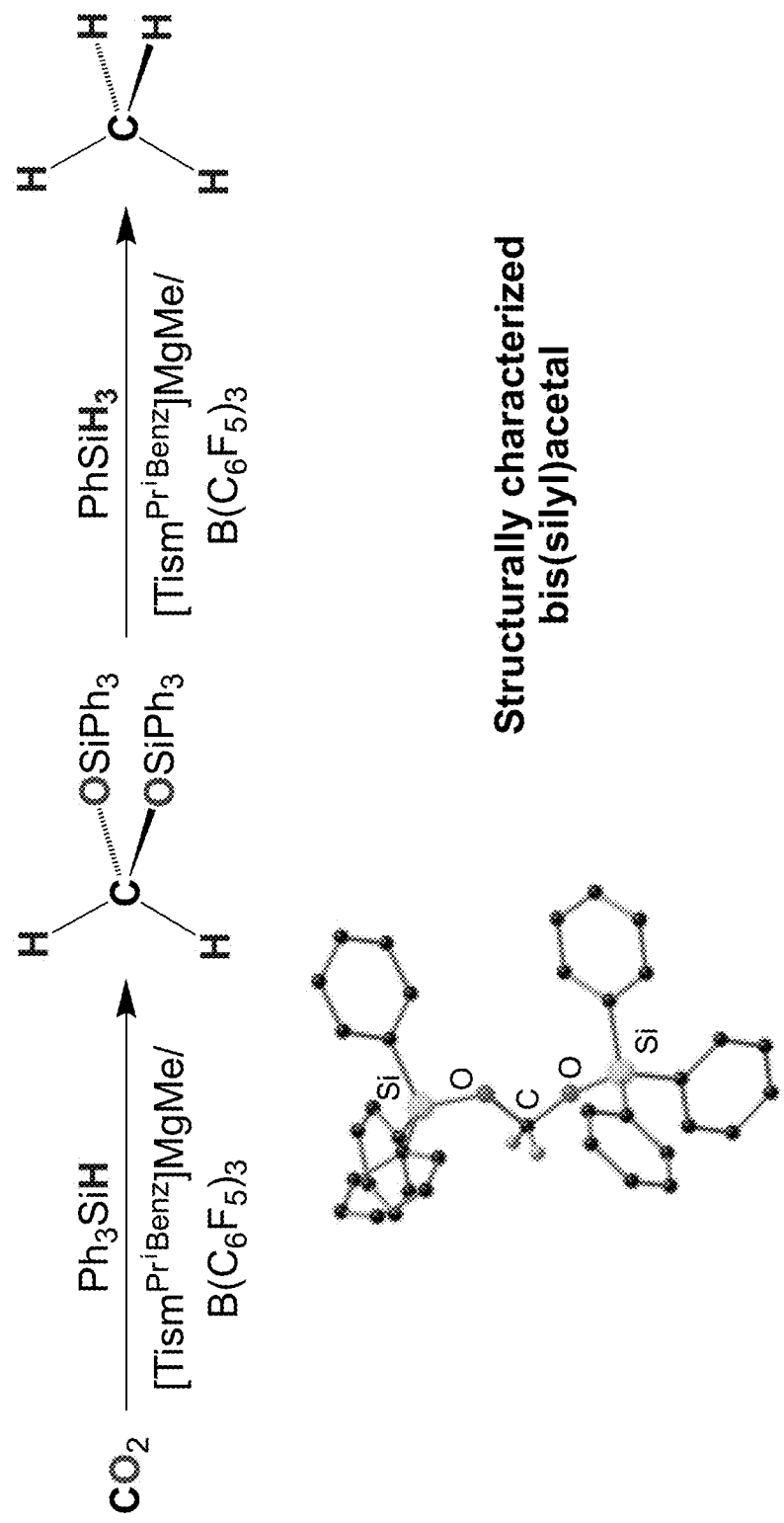
FIG. 1 shows the reactions that reduce $CO_2$ to a bis(silyl) acetal and then to methane.

One embodiment of the present disclosure is a method for preparing formaldehyde from carbon dioxide, comprising the steps of: (a) obtaining a bis(silyl)acetal; and (b) generating formaldehyde by any one of the following: (i) adding a fluoride compound to a solution of the bis(silyl)acetal in a solvent; or (ii) reaction of the bis(silyl)acetal with water in a solvent; or (iii) reaction of the bis(silyl)acetal with an acid in a solvent. In some embodiments, the formaldehyde can be generated by methods other than those described above.

In some embodiments, the bis(silyl)acetal is generated by the reaction between carbon dioxide and a silane in the presence of a compound prepared from a multidentate ligand having the structure of:

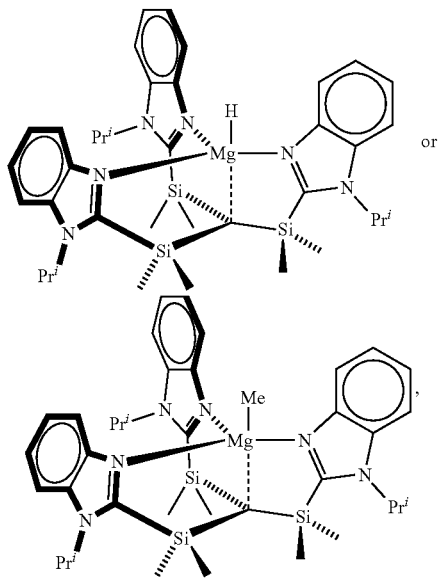

and $B(C_6F_5)_3$, wherein the silane is $R_3SiH$ and R is selected from H, alkyl and aryl. In some embodiments, the bis(silyl)acetal is $H_2C(OSiPh_3)_2$. In some embodiments, the formaldehyde generated is anhydrous.

In some embodiments, the fluoride compound is selected from CsF, KF, NaF, LiF, tetra(n-butyl)ammonium fluoride, and trimethyltin fluoride. In some embodiments, the fluoride compound is CsF. In other embodiments, the fluoride compound may be selected from other well know fluoride compounds, so long as such fluoride compound is effective to carry out the reaction.

In the present disclosure, the solvent in each of steps (b)(i)-(b)(iii) is independently selected, and the solvent may refer to the same solvent or a different solvent as required by the particular reaction. For example, in some embodiments, the solvent in each of step (b)(i), step (b)(ii) and step (b)(iii) is independently selected from acetonitrile, acetone, DMF, DMSO, γ-Butyrolactone, ethers, aromatic solvents and aliphatic solvents. In the present disclosure, any combination of solvents may be selected. In some embodiments, the solvent in step (b)(i) is acetonitrile, the solvent in step (b)(ii) is DMSO, and the solvent in step (b)(iii) is acetonitrile. In other embodiments, the solvent may be selected from other well know solvent, so long as such solvent is effective to carry out the reaction.

In some embodiments, the acid is selected from sulfuric acid, nitric acid, hydrohalic acids, carboxylic acid and phosphoric acid. In some embodiments, the acid is sulfuric acid. In other embodiments, the acid may be selected from other well know acids, so long as such acid is effective to carry out the reaction Another embodiment of the present disclosure is a method for completing a transformation that involves formaldehyde by substituting formaldehyde with a bis(silyl)acetal.

In some embodiments, the bis(silyl)acetal is generated by the reaction between carbon dioxide and a silane in the presence of a compound prepared from a multidentate ligand having the structure of:

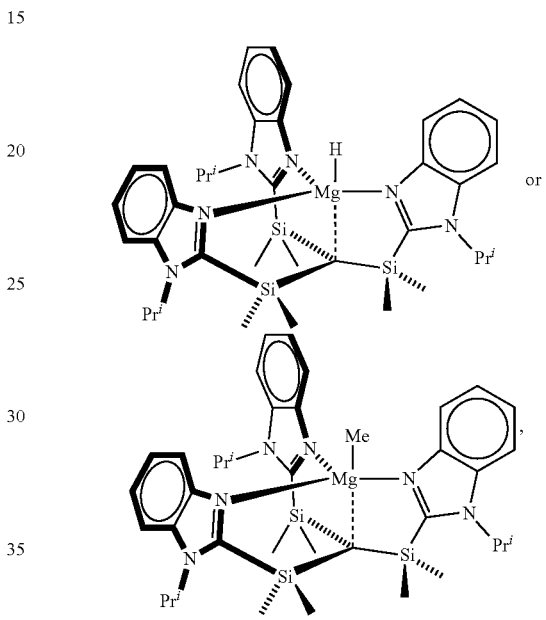

and $B(C_6F_5)_3$, wherein the silane is $R_3SiH$ and R is selected from H, alkyl and aryl. In some embodiments, the bis(silyl)acetal is $H_2C(OSiPh_3)_2$. In some embodiments, the transformation is selected from: the formation of a terminal olefin in a Wittig reaction, the synthesis of hexamine from ammonia, the Pictet Spengler reaction for the preparation of heterocycles, and the synthesis of benzazoles.

A further embodiment of the present disclosure is a method for incorporating carbon derived from carbon dioxide into a complex organic molecule derived from formaldehyde, comprising the steps of: (a) obtaining a bis(silyl)acetal by the reaction between carbon dioxide and a silane in the presence of a compound prepared from a multidentate ligand having the structure of:

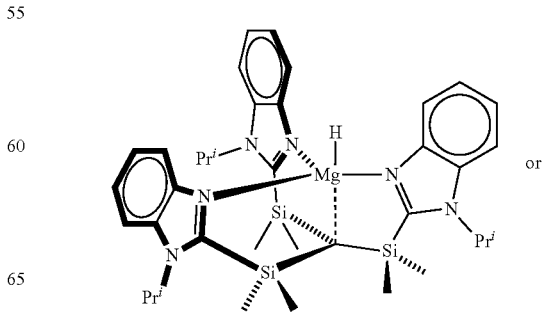

-continued

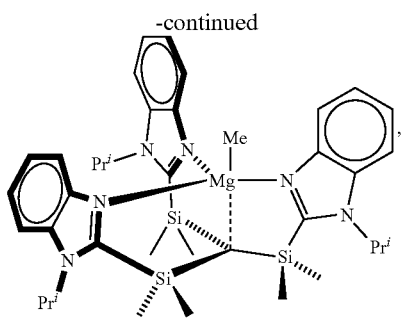

and $B(C_6F_5)_3$, wherein the silane is $R_3SiH$ and R is selected from H, alkyl and aryl; and (b) substituting formaldehyde with the bis(silyl)acetal in a reaction that generates the complex organic molecule.

In some embodiments, the bis(silyl)acetal is $H_2C(OSiPh_3)_2$. In some embodiments, the reaction is selected from: the formation of a terminal olefin in a Wittig reaction, the synthesis of hexamine from ammonia, the Pictet Spengler reaction for the preparation of heterocycles, and the synthesis of benzazoles. In some embodiments, the bis(silyl)acetal generated in step (a) is isotope-labeled by using isotope-labeled carbon dioxide and/or isotope-labeled silane in the reaction mixture. In some embodiments, the carbon dioxide is isotope-labeled using $^{11}C$, $^{13}C$, or $^{14}C$. In some embodiments, the silane is isotope-labeled using $^2H$ or $^3H$. In some embodiments, the bis(silyl)acetal generated in step (a) is isotope-labeled by using $^{13}C$-labeled carbon dioxide and/or $^2H$-labeled silane in the reaction mixture.

Still another embodiment of the present disclosure is a method for generating an isotopologue of a complex organic molecule derived from formaldehyde, comprising the steps of: (a) generating isotope-labeled bis(silyl)acetal according to the methods disclosed herein by using isotope-labeled carbon dioxide and/or isotope-labeled silane in the reaction mixture; and (b) generating the isotopologue of the complex organic molecule by using the isotope-labeled bis(silyl)acetal obtained in step (a).

In some embodiments, the carbon dioxide is isotope-labeled using $^{11}C$, $^{13}C$, or $^{14}C$, although other labeled isotopes of carbon are within the scope of the present disclosure. In some embodiments, the silane is isotope-labeled using $^2H$ or $^3H$, although other labeled isotopes of hydrogen are within the scope of the present disclosure. In some embodiments, the bis(silyl)acetal generated in step (a) is isotope-labeled by using $^{13}C$-labeled carbon dioxide and/or $^2H$-labeled silane in the reaction mixture.

In some embodiments, the isotopologue generated is a probe for positron emission tomography (PET). Non-limiting examples of a probe for PET include [$^{11}C$] Acetate, [$^{11}C$] 25B-NBOMe (Cimbi-36), [$^{11}C$] Carfentanil, [$^{11}C$] DASB, [$^{11}C$] DTBZ, [$^{11}C$] ME@HAPTHI, [$^{11}C$] Pittsburgh compound B, [$^{11}C$] Raclopride, [$^{11}C$] Verapamil, [$^{11}C$] N-Methylspiperone, [$^{11}C$] Martinostat, [$^{11}C$] Methionine, [$^{11}C$] choline, and combinations thereof. PET probes generated according to the methods of this disclosure may be used as medical and research tools. For example, PET probes generated according to the methods of this disclosure may be used in clinical oncology applications, including tumor imaging and the search for metastases. Additional applications for PET probes of the present disclosure include neuroimaging, cardiovascular imaging, imaging infections, pharmacokinetic imaging, such as biodistribution studies, small animal imaging and musculoskeletal imaging.

The utility of the method of the present disclosure to synthesize isotopologues of formaldehyde is of significance because it provides a means to incorporate isotopic labels into molecules with biological and medicinal applications. In this regard, the isotopic labeling of a drug candidate provides a critical means to evaluate its absorption, distribution, metabolism and excretion properties (Elmore, 2009; Isin et al. 2012). Deuterium labeled modifications of drugs are also of current interest due to enhanced stability by virtue of the kinetic isotope effect (Atzrodt et al. 2018; Gant, 2014; Allen et al. 2010), while the incorporation of $^{13}C$ labels is of benefit to the application of clinical $^{13}C$ magnetic resonance spectroscopy (Valette et al. 2017) and for investigating metabolic networks (Chokkathukalam et al. 2014). Although carbon dioxide is considered to be the universal precursor for incorporating isotopic labels ($^{11}C$, $^{13}C$ and $^{14}C$) (Taddei and Gee, 2018; Del Vecchio et al. 2018; Kingston et al. 2019; Scott, 2009; Bragg et al. 2018), direct approaches are limited due to the aforementioned low reactivity of this molecule (Liger et al. 2015; Haywood et al. 2018; Antoni, 2015). For example, the synthesis of isotopically labeled formaldehyde from $CO_2$ using $LiAlH_4$ is hampered by the formation of considerable quantities of labeled formic acid and methanol (Roeda and Crouzel, 2001). The conversion of carbon dioxide into isotopically labeled formaldehyde as disclosed herein is, thus, of considerable interest since its greater reactivity facilitates the incorporation of a carbon label (Dahl et al. 2018; Maxwell, 2018; Dao et al. 2015; Burgos-Barragan et al. 2017; Roberson and Macnaughtan, 2014; Boersema et al. 2009; Hsu et al. 2006).

An illustration that isotopically labeled formaldehyde derived from $CO_2$ via the bis(silyl)acetal, $H_2C(OSiPh_3)_2$, can be employed in this manner is provided by the formation of $^{13}C$ labeled methyl acrylate $MeOC(O)C(H)^{13}CH_2$. Specifically, $MeOC(O)C(H)^{13}CH_2$ is obtained by reaction of $MeOC(O)C(H)PPh_3$ with $^{13}CH_2O$ generated in situ by addition of CsF to $H_2^{13}C(OSiPh_3)_2$, which is more direct than the literature method which employs $^{13}CH_3I$ rather than $^{13}CO_2$. Likewise, $MeOC(O)C(H)^{13}CD_2$ and $MeOC(O)C(H)CD_2$ were also obtained by this new approach.

In view of the fact that heterocycles play an important role in pharmaceuticals, much effort has been directed towards the formation of isotopically labeled derivatives, and developing routes that utilize $CO_2$ has been emphasized. Therefore, another embodiment of the present disclosure is a method of reacting $D_2C(OSiPh_3)_2$ with N-methyl-1,2-phenylenediamine in DMSO which affords N-methylbenzimidazole-$d_1$. In addition, $^2H$ NMR spectroscopy demonstrates that the formal oxidation of the [$CH_2$] moiety is achieved by the formation of water, in accord with the aforementioned ability of DMSO to act as an oxidizing agent.

Another embodiment of the present disclosure is a probe obtained by the methods disclosed herein.

In some embodiments, the probe is a diagnostic probe. In some embodiments, the probe is a positron emission tomography (PET) probe.

Another embodiment of the present disclosure is a method for carrying out a chemical reaction with a formaldehyde surrogate comprising replacing formaldehyde in the chemical reaction with a bis(silyl)acetal.

In some embodiments, the bis(silyl)acetal is $H_2C(OSiPh_3)_2$.

In some embodiments, the chemical reaction involves formation of bonds selected from C—C, C—N, C—O and C—S, the formation of heterocycles, and combinations thereof. In some embodiments, the chemical reaction involves those depicted in FIGS. 3-5.

The following examples are provided to further illustrate the methods of the present disclosure. These examples are illustrative only and are not intended to limit the scope of the disclosure in any way.

EXAMPLES

Example 1

Selective Reduction of $CO_2$ to Formaldehyde at Room Temperature

Figure 2:
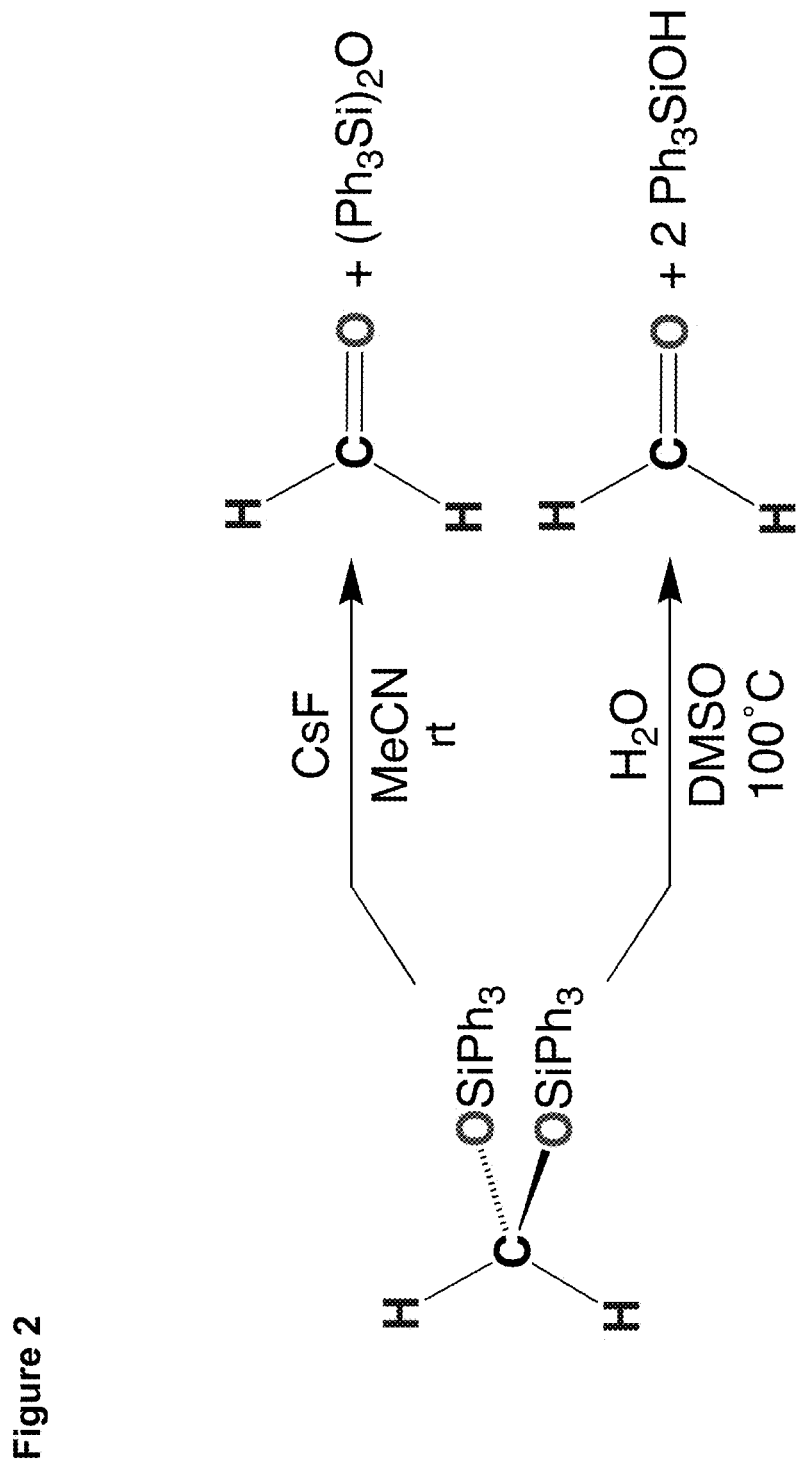
FIG. 2 shows the reactions that convert the bis(silyl)acetal to formaldehyde.

Both [Tism$^{Pr^jBenz}$]MgH and the methyl complex, [Tism$^{Pr^jBenz}$]MgMe can be used in conjunction with $B(C_6F_5)_3$ to form the bis(silyl)acetal, $H_2C(OSiPh_3)_2$, on a multigram scale in a selective manner. [Tism$^{Pr^jBenz}$]MgH and [Tism$^{Pr^jBenz}$]MgMe were prepared as previously described in Parkin, et al., U.S. application Ser. No. 16/359,136 filed Mar. 20, 2019 (U.S. Patent Application Publication No. 20190291088, published on Sep. 26, 2019), which application, including the method, is expressly incorporated herein by reference. $H_2C(OSiPh_3)_2$ can be reduced to methane by $PhSiH_3$, providing a clear indication of how selectivity is influenced by the choice of silane (FIG. 1). While bis(silyl)acetals are often referred to as possessing the "formaldehyde level", it must be emphasized that they are not formaldehyde. $H_2C(OSiPh_3)_2$ can, however, be converted immediately to formaldehyde by CsF (FIG. 2).

The selective reduction of $CO_2$ to formaldehyde is not possible because subsequent reduction to methanol is strongly exothermic. Therefore, formaldehyde is obtained industrially by the partial oxidation of methanol (the Formox process):

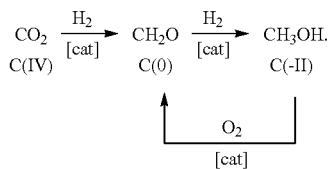

The conversion of $CO_2$ to formaldehyde via the bis(silyl)acetal is a direct, room temperature, single vessel transformation that manages redox changes in an efficient manner (see below). Isotopologues (e.g., $^{12}C/^{11}C$, $^{12}C/^{13}C$ and $^1H/^2H$, $^1H/^3H$) may also be readily obtained.

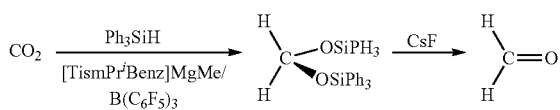

Figure 3:
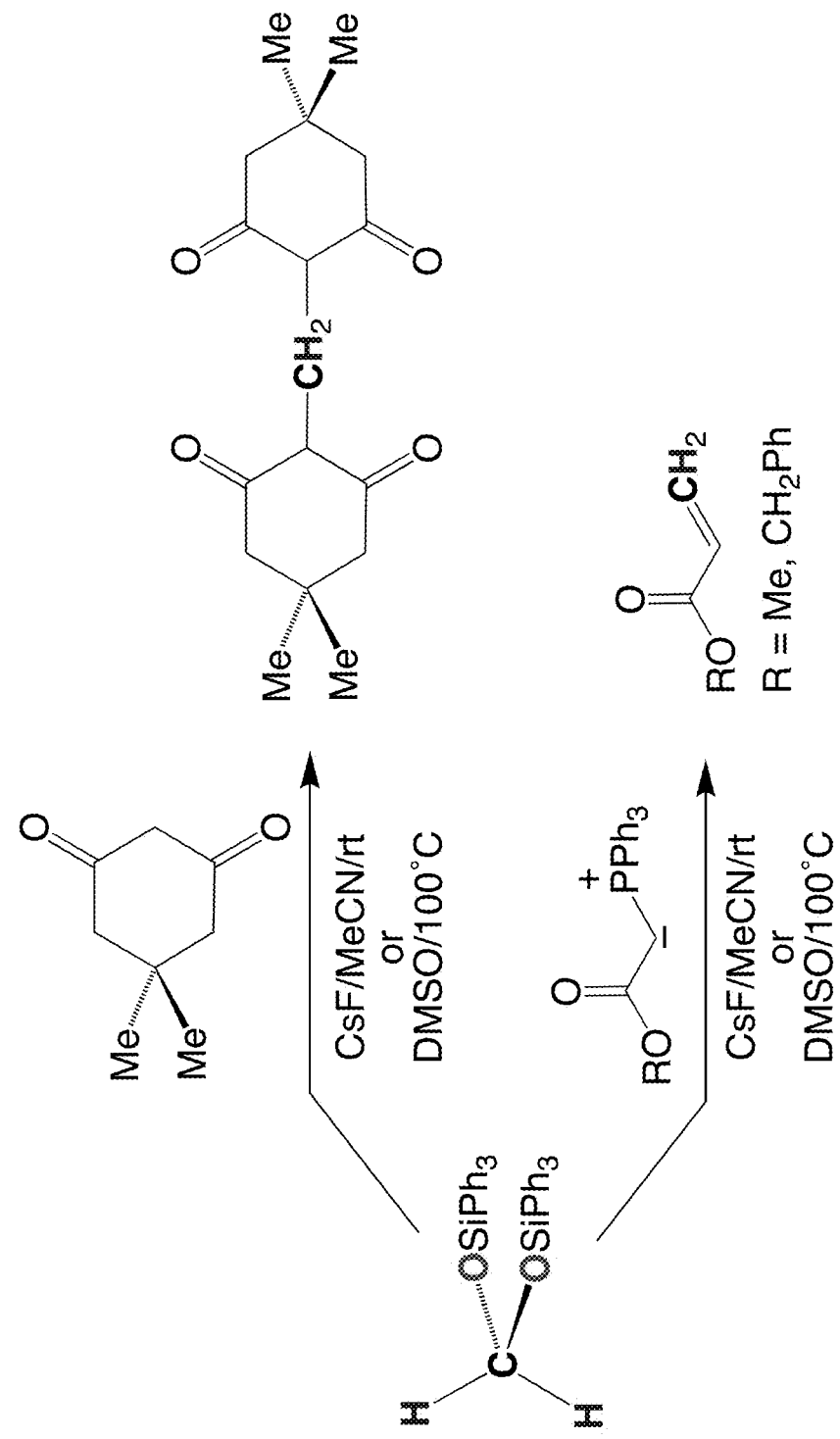
FIG. 3 shows the formation of C—C bonds using the bis(silyl)acetal as a formaldehyde surrogate.
Figure 4:
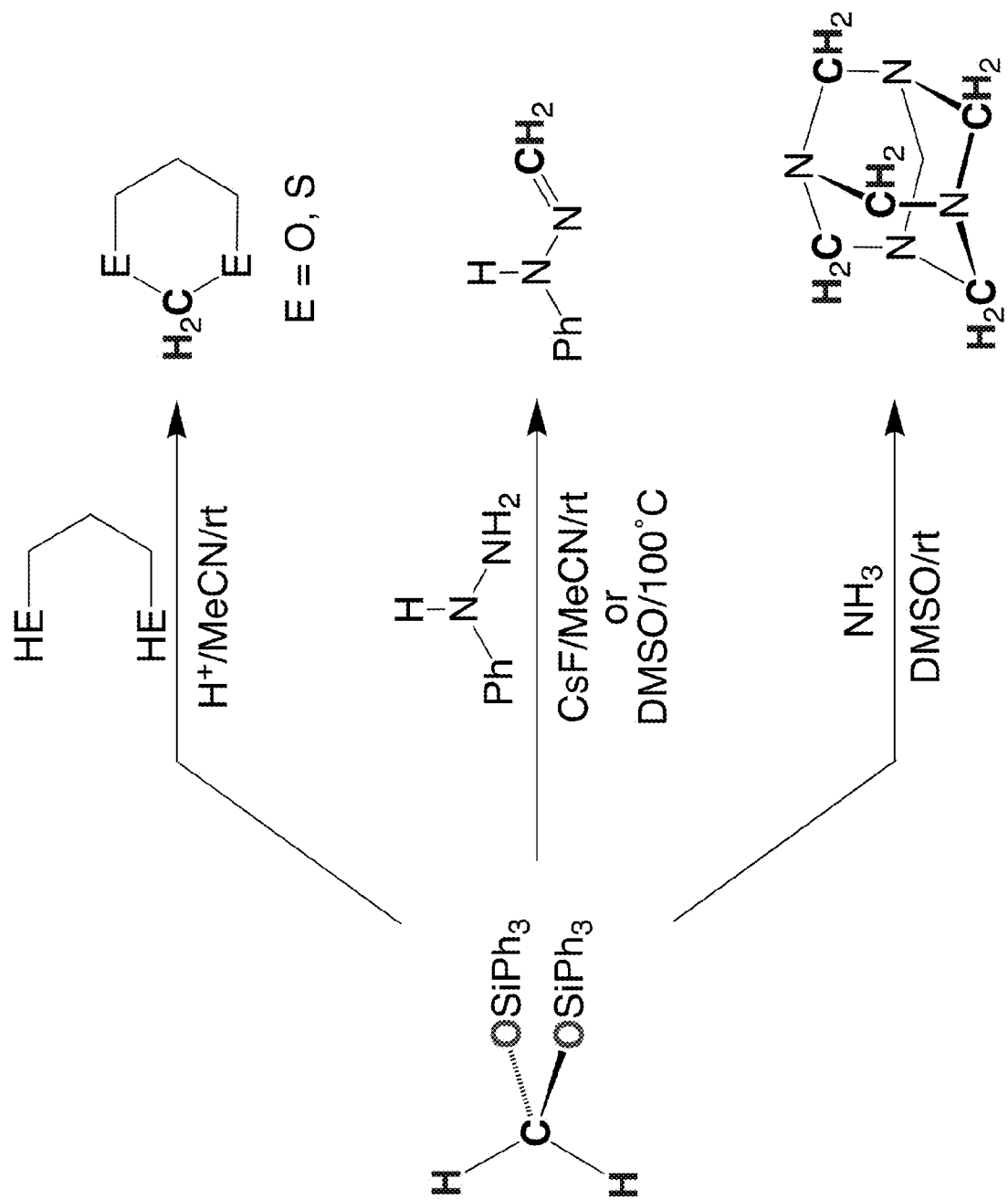
FIG. 4 shows the formation of C—N, C—O and C—S bonds using the bis(silyl)acetal as a formaldehyde surrogate.
Figure 5:
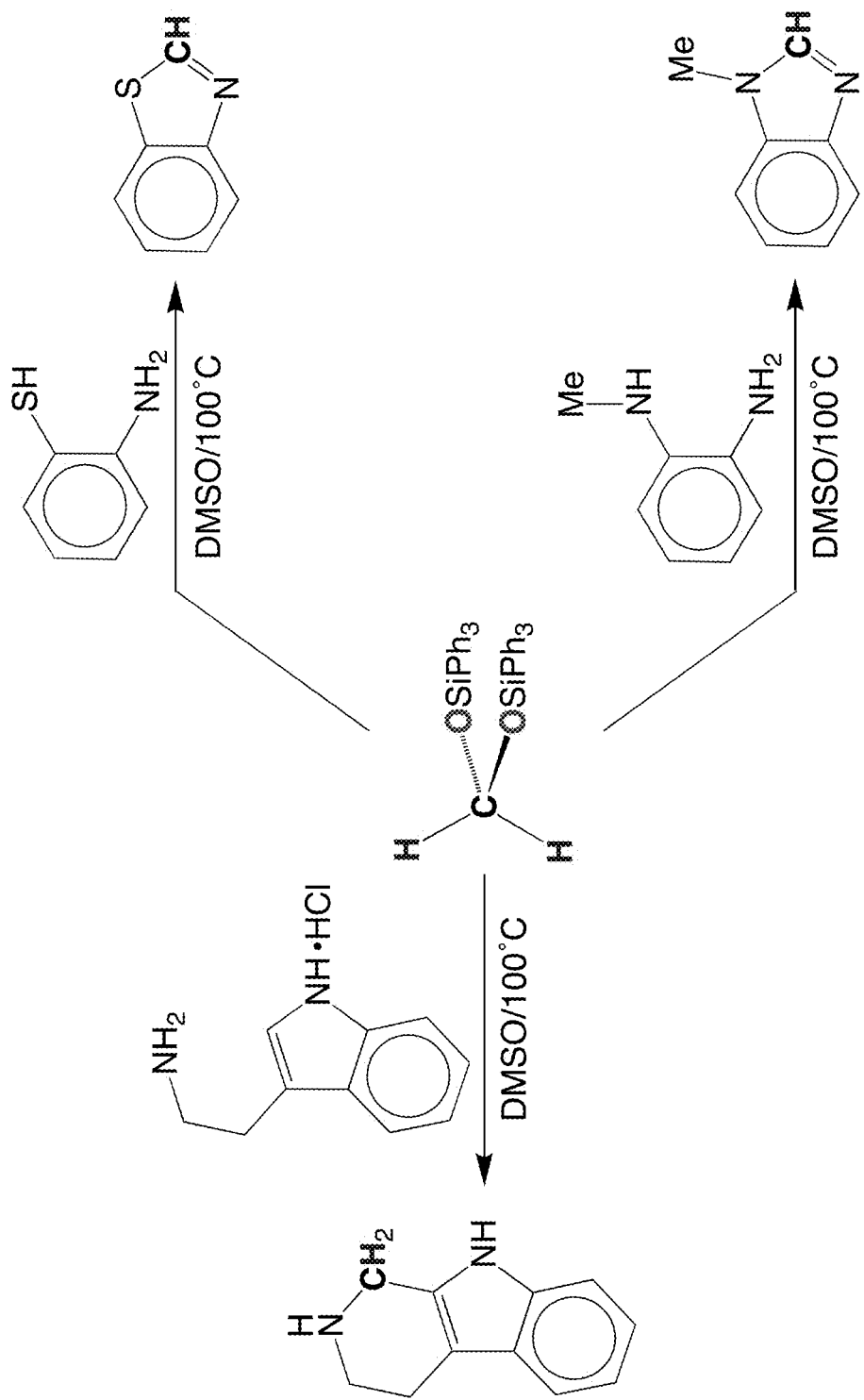
FIG. 5 shows the formation of heterocycles using the bis(silyl)acetal as a formaldehyde surrogate.

$H_2C(OSiPh_3)_2$ can be readily used as a surrogate for fomaldehyde, thereby providing a means to incorporate carbon derived from $CO_2$ into a variety of complex organic molecules (FIGS. 3-5). Isotopologues can also be readily obtained.

Example 2

Preparation of PET Probes

Positron-emission tomography (PET) is a nuclear medicine functional imaging technique that is used to observe metabolic processes in the body as an aid to the diagnosis of disease. The system detects pairs of gamma rays emitted indirectly by a positron-emitting radioligand, which is introduced into the body on a biologically active molecule called a radioactive tracer. Different ligands are used for different imaging purposes, depending on what the radiologist/researcher wants to detect. The methods described in the present disclosure can be used to prepare an isotopologue of a complex organic molecule such as a radiotracer to be used in PET scanning applications.

For example, to prepare [$^{11}C$] Acetate, a commonly used PET radiotracer in cardiology and oncology, one can first generate isotope-labeled formaldehyde using $^{11}C$-labeled carbon dioxide according to methods disclosed herein. Next, [$^{11}C$]-labeled ethanol can be obtained via a Grignard reaction, e.g.,

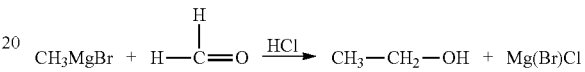

The resultant ethanol can then be oxidized to obtain [$^{11}C$] Acetate.

DOCUMENTS CITED

1. Allen, P. H.; Hickey, M. J.; Kingston, L. P.; Wilkinson, D. J. "Metal-catalysed isotopic exchange labelling: 30 years of experience in pharmaceutical R&D" *J. Label. Compd. Radiopharm.* 2010, 53, 731-738.

2. Antoni, G. "Development of carbon-11 labelled PET tracers—Radiochemical and technological challenges in a historic perspective" *J. Label. Compd. Radiopharm.* 2015, 58, 65-72.

3. Aresta, M., Carbon Dioxide as Chemical Feedstock. (2010) Wiley-VCH Verlag GmbH & Co. KGaA, online ISBN: 9783527629916

4. Atzrodt, J.; Derdau, V.; Kerr, W. J.; Reid, M. "Deuterium- and tritium-labelled compounds: Applications in the life sciences" *Angew. Chem. Int. Edit.* 2018, 57, 1758-1784.

5. Boersema, P. J.; Raijmakers, R.; Lemeer, S.; Mohammed, S.; Heck, A. J. R. "Multiplex peptide stable isotope dimethyl labeling for quantitative proteomics" *Nat. Protoc.* 2009, 4, 484-494.

6. Bragg, R. A.; Sardana, M.; Artelsmair, M.; Elmore, C. S. "New trends and applications in carboxylation for isotope chemistry" *J. Label. Compd. Radiopharm.* 2018, 61, 934-948.

7. Burgos-Barragan, G.; Wit, N.; Meiser, J.; Dingler, F. A.; Pietzke, M.; Mulderrig, L.; Pontel, L. B.; Rosado, I. V.; Brewer, T. F.; Cordell, R. L.; Monks, P. S.; Chang, C. J.; Vazquez, A.; Patel, K. J. "Mammals divert endogenous genotoxic formaldehyde into one-carbon metabolism" *Nature* 2017, 548, 549-554.

8. Chokkathukalam, A.; Kim, D.-H.; Barrett, M. P.; Breitling, R.; Creek, D. J. "Stable isotope-labeling studies in metabolomics: new insights into structure and dynamics of metabolic networks" *Bioanalysis* 2014, 6, 511-524.

9. Dahl, K.; Halldin, C.; Schou, M. "New methodologies for the preparation of carbon-11 labeled radiopharmaceuticals" *Clin. Transl. Imaging* 2017, 5, 275-289.

10. Dao, H. T.; Li, C.; Michaudel, Q.; Maxwell, B. D.; Baran, P. S. "Hydromethylation of unactivated olefins" *J. Am. Chem. Soc.* 2015, 137, 8046-8049.

11. Del Vecchio, A.; Caille, F.; Chevalier, A.; Loreau, O.; Horkka, K.; Halldin, C.; Schou, M.; Camus, N.; Kessler, P.;

Kuhnast, B.; Taran, F.; Audisio, D. "Late-stage isotopic carbon labeling of pharmaceutically relevant cyclic ureas directly from $CO_2$" *Angew. Chem. Int. Edit.* 2018, 57, 9744-9748.

12. Elmore, C. S. "The use of isotopically labeled compounds in drug discovery" *Ann. Rep. Med. Chem.* 2009, 44, 515-534.

13. Fraga, H., Santos, J A., Malheiro, A C., Oliveira, A A., Jones, G V., Santos, J. A., Malheiro, A. C., Oliveira, A. A., Moutinho-Pereira, J., Jones, G. V., Climatic suitability of Portuguese grapevine varieties and climate change adaptation. *Int. J. Climatol.* (2015)

14. Gant, T. G. "Using deuterium in drug discovery: Leaving the label in the drug" *J. Med. Chem.* 2014, 57, 3595-3611.

15. Haywood, T.; Cesarec, S.; Kealey, S.; Plisson, C.; Miller, P. W. "Ammonium [$^{11}$C]thiocyanate: revised preparation and reactivity studies of a versatile nucleophile for carbon-11 radiolabelling" *MedChemComm* 2018, 9, 1311-1314.

16. Hsu, J. L.; Huang, S. Y.; Chen, S. H. "Dimethyl multiplexed labeling combined with microcolumn separation and MS analysis for time course study in proteomics" *Electrophoresis* 2006, 27, 3652-3660.

17. Isin, E. M.; Elmore, C. S.; Nilsson, G. N.; Thompson, R. A.; Weidolf, L. "Use of radiolabeled compounds in drug metabolism and pharmacokinetic studies" *Chem. Res. Toxicol.* 2012, 25, 532-542.

18. Kingston, C.; Wallace, M. A.; Allentoff, A. J.; deGruyter, J. N.; Chen, J. S.; Gong, S. X.; Bonacorsi, S.; Baran, P. S. "Direct carbon isotope exchange through decarboxylative carboxylation" *J. Am. Chem. Soc.* 2019, 141, 774-779.

19. Liger, F.; Eijsbouts, T.; Cadarossanesaib, F.; Tourvieille, C.; Le Bars, D.; Billard, T. "Direct [$^{11}$C]methylation of amines from [$^{11}$C]$CO_2$ for the synthesis of PET radiotracers" *Eur. J. Org. Chem.* 2015, 6434-6438.

20. Liu, Q., Wu, L., Jackstell, R. et al. Using carbon dioxide as a building block in organic synthesis. *Nat Commun* 6, 5933 (2015).

21. Maxwell, B. D. "New radical methods for the potential synthesis of carbon-13 and carbon-14 labeled complex products" *J. Label. Compd. Radiopharm.* 2018, 61, 1024-1035.

22. Roberson, K. J.; Macnaughtan, M. A. "Review of methods to assign the nuclear magnetic resonance peaks of reductively methylated proteins" *Anal. Biochem.* 2014, 466, 76-82.

23. Roeda, D.; Crouzel, C. "[$^{11}$C]Formaldehyde revisited: Considerable concurrent [$^{11}$C]formic acid formation in the low-temperature conversion of [$^{11}$C]carbon dioxide into [$^{11}$C]formaldehyde" *Appl. Radiat. Isot.* 2001, 54, 935-939.

24. Scott, P. J. H. "Methods for the incorporation of carbon-11 to generate radiopharmaceuticals for pet imaging" *Angew. Chem. Int. Edit.* 2009, 48, 6001-6004.

25. Taddei, C.; Gee, A. D. "Recent progress in [C-11] carbon dioxide ([C-11]CO2) and [C-11]carbon monoxide ([C-11]CO) chemistry" *J. Label. Compd. Radiopharm.* 2018, 61, 237-251.

26. Valette, J.; Tiret, B.; Boumezbeur, F. "Experimental strategies for in vivo $^{13}$C NMR spectroscopy" *Anal. Biochem.* 2017, 529, 216-228.

All documents cited in this application are hereby incorporated by reference as if recited in full herein.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

What is claimed is:

1. A method for preparing formaldehyde, comprising the steps of:
   (a) obtaining a bis(silyl)acetal; and
   (b) generating formaldehyde by any one of the following:
      adding a fluoride compound to a solution of the bis(silyl)acetal in a solvent; or
      (ii) reacting the bis(silyl)acetal with water in a solvent; or
      (iii) reacting the bis(silyl)acetal with an acid in a solvent.

2. The method of claim 1, wherein the bis(silyl)acetal is generated by the reaction between carbon dioxide and a silane in the presence of a compound prepared from a multidentate ligand having the structure of:

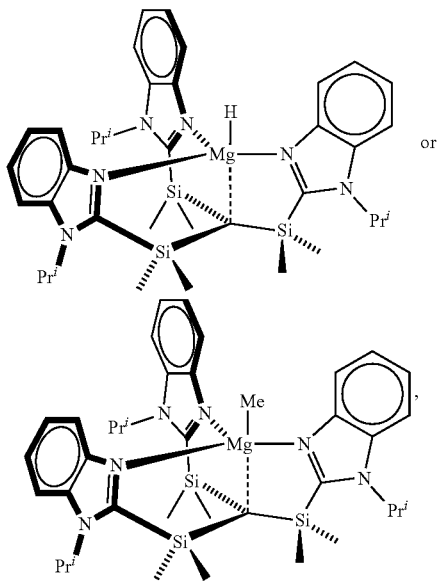

and $B(C_6F_5)_3$,
wherein the silane is $R_3SiH$ and R is selected from H, alkyl and aryl.

3. The method of claim 1, wherein the bis(silyl)acetal is $H_2C(OSiPh_3)_2$.

4. The method of claim 1, wherein the formaldehyde generated is anhydrous.

5. The method of claim 1, wherein the fluoride compound is selected from CsF, KF, NaF, LiF, tetra(n-butyl)ammonium fluoride, and trimethyltin fluoride.

6. The method of claim 1, wherein the fluoride compound is CsF.

7. The method of claim 1, wherein the solvent in each of step (b)(i), step (b)(ii) and step (b)(iii) is independently selected from acetonitrile, acetone, DMF, DMSO, γ-Butyrolactone, ethers, aromatic solvents and aliphatic solvents.

8. The method of claim 1, wherein the solvent in step (b)(i) is acetonitrile, the solvent in step (b)(ii) is DMSO, and the solvent in step (b)(iii) is acetonitrile.

9. The method of claim 1, wherein the acid is selected from sulfuric acid, nitric acid, hydrohalic acids, carboxylic acid and phosphoric acid.

10. The method of claim 1, wherein the acid is sulfuric acid.

11. A method for completing a transformation that involves formaldehyde, comprising substituting formaldehyde with a bis(silyl)acetal.

12. The method of claim 11, wherein the bis(silyl)acetal is generated by the reaction between carbon dioxide and a silane in the presence of a compound prepared from a multidentate ligand having the structure of:

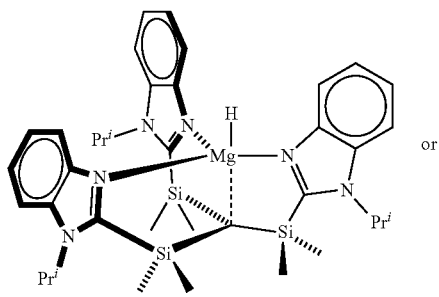

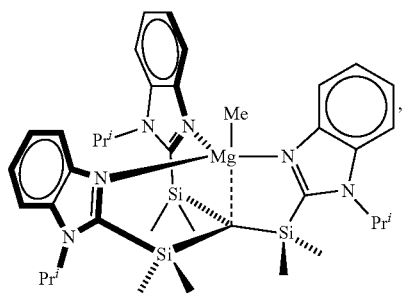

and B(C$_6$F$_5$)$_3$,
wherein the silane is R$_3$SiH and R is selected from H, alkyl and aryl.

13. The method of claim 11, wherein the bis(silyl)acetal is H$_2$C(OSiPh$_3$)$_2$.

14. The method of claim 11, wherein the transformation is selected from: the formation of a terminal olefin in a Wittig reaction, the synthesis of hexamine from ammonia, the Pictet Spengler reaction for the preparation of heterocycles, and the synthesis of benzazoles.

15. A method for incorporating carbon derived from carbon dioxide into a complex organic molecule derived from formaldehyde, comprising the steps of:
(a) obtaining a bis(silyl)acetal by the reaction between carbon dioxide and a silane in the presence of a compound prepared from a multidentate ligand having the structure of:

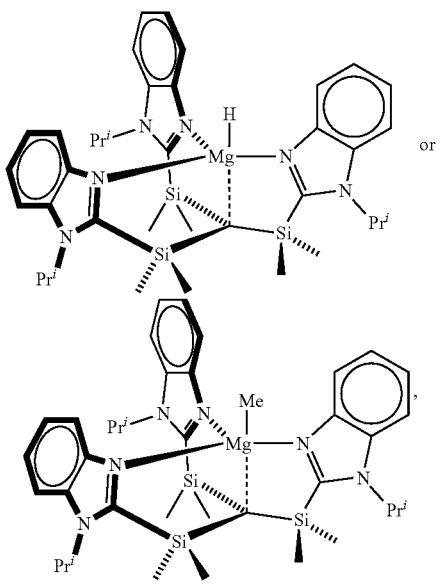

and B(C$_6$F$_5$)$_3$, wherein the silane is R$_3$SiH and R is selected from H, alkyl and aryl; and
(b) substituting formaldehyde with the bis(silyl)acetal in a reaction that generates the complex organic molecule.

16. The method of claim 15, wherein the bis(silyl)acetal is H$_2$C(OSiPh$_3$)$_2$.

17. The method of claim 15, wherein the reaction is selected from:
the formation of a terminal olefin in a Wittig reaction, the synthesis of hexamine from ammonia, the Pictet Spengler reaction for the preparation of heterocycles, and the synthesis of benzazoles.

18. The method of claim 15, wherein the bis(silyl)acetal generated in step (a) is isotope-labeled by using isotope-labeled carbon dioxide and/or isotope-labeled silane in the reaction mixture.

19. The method of claim 18, wherein the carbon dioxide is isotope-labeled using $^{11}$C, $^{13}$C, or $^{14}$C.

20. The method of claim 18, wherein the silane is isotope-labeled using $^2$H or $^3$H.

21. The method of claim 15, wherein the bis(silyl)acetal generated in step (a) is isotope-labeled by using $^{13}$C-labeled carbon dioxide and/or $^2$H-labeled silane in the reaction mixture.

22. A method for generating an isotopologue of a complex organic molecule derived from formaldehyde, comprising the steps of:
(a) generating isotope-labeled bis(silyl)acetal according to the method of claim 2 by using isotope-labeled carbon dioxide and/or isotope-labeled silane in the reaction mixture; and
(b) generating the isotopologue of the complex organic molecule by using the isotope-labeled bis(silyl)acetal obtained in step (a).

23. The method of claim 22, wherein the carbon dioxide is isotope-labeled using $^{11}$C, $^{13}$C, or $^{14}$C.

24. The method of claim 22, wherein the silane is isotope-labeled using $^2$H or $^3$H.

25. The method of claim 22, wherein the bis(silyl)acetal generated in step (a) is isotope-labeled by using $^{13}$C-labeled carbon dioxide and/or $^2$H-labeled silane in the reaction mixture.

26. The method of claim 22, wherein the isotopologue generated is a probe for positron emission tomography (PET).

27. The method of claim 26, wherein the probe for PET is selected from the group consisting of [$^{11}$C] Acetate, [$^{11}$C] 25B-NBOMe (Cimbi-36), [$^{11}$C] Carfentanil, [$^{11}$C] DASB, [$^{11}$C] DTBZ, [$^{11}$C] ME@HAPTHI, [$^{11}$C] Pittsburgh compound B, [$^{11}$C] Raclopride, [$^{11}$C] Verapamil, [$^{11}$C] N-Methylspiperone, [$^{11}$C] Martinostat, [$^{11}$C] Methionine, [$^{11}$C] choline, and combinations thereof.

28. A method for carrying out a chemical reaction with a formaldehyde surrogate comprising replacing formaldehyde in the chemical reaction with a bis(silyl)acetal.

29. The method of claim 28, wherein the bis(silyl)acetal is $H_2C(OSiPh_3)_2$.

30. The method of claim 28, wherein the chemical reaction involves formation of bonds selected from C—C, C—N, C—O and C—S, the formation of heterocycles, and combinations thereof.

\* \* \* \* \*